(12) United States Patent
Rietzel

(10) Patent No.: US 8,897,417 B2
(45) Date of Patent: Nov. 25, 2014

(54) METHOD AND DEVICE FOR PLANNING A TREATMENT

(75) Inventor: Eike Rietzel, Darmstadt (DE)

(73) Assignee: Siemens Aktiengesellschaft, München (DE)

( * ) Notice: Subject to any disclaimer, the term of this patent is extended or adjusted under 35 U.S.C. 154(b) by 1489 days.

(21) Appl. No.: 12/094,903

(22) PCT Filed: Nov. 23, 2006

(86) PCT No.: PCT/EP2006/068788
§ 371 (c)(1),
(2), (4) Date: May 23, 2008

(87) PCT Pub. No.: WO2007/060187
PCT Pub. Date: May 31, 2007

(65) Prior Publication Data
US 2008/0292158 A1   Nov. 27, 2008

Related U.S. Application Data

(60) Provisional application No. 60/740,129, filed on Nov. 28, 2005.

(30) Foreign Application Priority Data
Nov. 28, 2005   (DE) .......................... 10 2005 056 701

(51) Int. Cl.
*A61N 5/10* (2006.01)
*G06F 19/00* (2011.01)

(52) U.S. Cl.
CPC ............ *A61N 5/103* (2013.01); *G06F 19/3443* (2013.01); *G06F 19/363* (2013.01); *G06F 19/321* (2013.01)
USPC ........................................... 378/65; 378/207

(58) Field of Classification Search
USPC ................................................... 378/65, 207
See application file for complete search history.

(56) References Cited

U.S. PATENT DOCUMENTS

2004/0101105 A1*   5/2004   Segawa et al. ................. 378/108
2004/0165696 A1*   8/2004   Lee .................................. 378/65

(Continued)

FOREIGN PATENT DOCUMENTS

GB          2 344 985 A      6/2000
WO    WO 2004/057515 A2     7/2004

(Continued)

OTHER PUBLICATIONS

Jaket et al., "Quality Assurance for a Treatment Planning System in Scanned Ion Beam Therapy," Medical Physics, vol. 27, No. 7, Jul. 2000, pp. 1588-1600. http://scitation.aip.org/getpdf/servlet/GetPDFServlet?filetype=pdf&id=MPHYA60000270000070015-88000001&idtype=cvip&prog=normal>thewholedocument.

(Continued)

*Primary Examiner* — Hoon Song
(74) *Attorney, Agent, or Firm* — Lempia Summerfield Katz LLC

(57) ABSTRACT

A device for planning an irradiation is provided. The device includes an evaluation module with an input for receiving input data, a memory and an output for outputting determined output data. The evaluation module is designed for using the input data that includes the type and number of the imaging units present, variables characterizing the tumor and/or variables characterizing the patient, in order to determine the output data that includes the type of the imaging unit, the frequency of use of the imaging unit and/or the parameters for setting the imaging unit to be used in the form of an imaging plan with the aid of a functional relationship, which is based on experience, stored in the memory.

12 Claims, 1 Drawing Sheet

(56) References Cited

U.S. PATENT DOCUMENTS

| | | |
|---|---|---|
| 2005/0041843 A1* | 2/2005 | Sawyer .................. 382/128 |
| 2005/0116172 A1 | 6/2005 | Trinkaus |
| 2005/0201516 A1 | 9/2005 | Ruchala et al. |
| 2005/0259779 A1 | 11/2005 | Abraham-Fuchs et al. |
| 2006/0153468 A1* | 7/2006 | Solf et al. .................. 382/254 |
| 2006/0198499 A1* | 9/2006 | Spies et al. .................. 378/207 |

FOREIGN PATENT DOCUMENTS

| | | |
|---|---|---|
| WO | WO 2005/021085 | 3/2005 |
| WO | WO 2005/031629 A1 | 4/2005 |

OTHER PUBLICATIONS

Written Opinion dated Mar. 2007.

International Search Report dated Mar. 21, 2007.

0. Jakel et al., "Quality assurance for a treatment planning system in scanned ion beam therapy", Medical Physics, vol. 27, Issue 7, pp. 1588-1600, Heidelberg, DE; XP-002423555, 2000.

German Office Action dated Jul. 18, 2006 for DE 10 2005 056 701.0-54 with English translation.

European Patent Office Action received Oct. 2009 for corresponding EP Case No. 06 807 833.6.

* cited by examiner

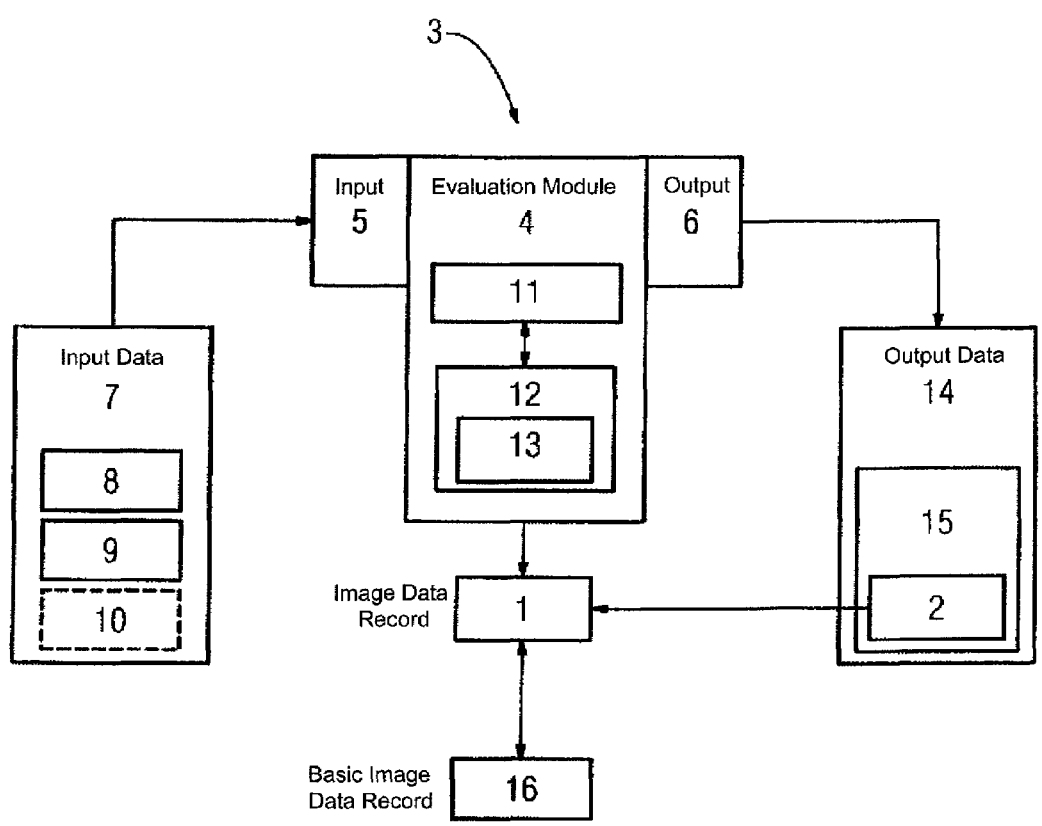

METHOD AND DEVICE FOR PLANNING A TREATMENT

The present patent document is a nationalization of PCT Application Serial Number PCT/EP2006/068788, filed Nov. 23, 2006, designating the United States, which is hereby incorporated by reference. This application also claims the benefit of DE 10 2005 056 701.0, Nov. 28, 2005, and U.S. provisional application 60/740,129, filed Nov. 28, 2005, both of which are also hereby incorporated by reference.

BACKGROUND

The present embodiments relate to a method and a device for planning particle and/or radiation therapy.

Before treating a patient suffering from a tumor by using particle and/or radiation therapy, it is customary to take (construct) a three-dimensional image (representation) with the aid of a medical imaging method, such as computed tomography, in order to visualize medical findings or physical and chemical phenomena. The three-dimensional image supplies information relating to the tumor, such as the tumor's position, size, stage of development, and the type of the tissue affected. The three-dimensional image serves as basic image data record for the therapy.

Further images of the tumor are taken during the therapy in order to monitor and to reposition the patient by an auxiliary imaging unit. A comparison of the further images with the basic image data record shows whether the patient needs be repositioned in order to ensure an acceptable treatment. The further images are generally two-dimensional images, such as X-ray images. A comparison with the 3D data of the basic image data record can be performed with the aid of the further images and, in particular, using images that are recorded with the aid of a number of radiation detector systems having mutually orthogonal axes. A system for three-dimensional volumetric imaging, such as cone beam computer tomographs, which are, in particular, already integrated in a treatment unit may be used to check the position and the success of the treatment. Other imaging methods could be used to check the position and the success of the treatment. For example, positron emission tomography is used for this purpose.

The customary mode of procedure for selecting the auxiliary imaging units and for setting the parameters that ensure suitably effective images with the aid of the auxiliary imaging unit is, however, in need of improvement. Both the selection of the parameters for imaging, and the selection of the auxiliary imaging units and frequency of the images are incumbent solely on the medical staff.

SUMMARY AND DESCRIPTION

The present embodiments may obviate one or more of the drawbacks or limitations inherent in the related art. For example, in one embodiment, automated planning of the treatment is provided.

In one embodiment, a method for planning a treatment of a patient's tumor in the case of particle and/or radiation therapy is provided. The method includes using input data that comprise the type and number of the imaging units present, variables characterizing the tumor and/or variables characterizing the patient, output data that comprise the type of the imaging unit, the frequency of use of the imaging unit and/or the parameters for setting the imaging unit to be used are determined for an imaging plan in an evaluation module by taking account of a functional relationship based on experience and stored in a memory.

In one embodiment, planning a treatment is largely automated such that the work sequence is much quicker and simpler, and a particularly high patient throughput is achieved. The method can be used to store a virtually unlimited quantity of information based on experience, which forms the basis for exacting calculations of a number of parameters and combinations of units.

The input data is logged in the evaluation module before the first session. This can be done, for example, via a keypad, a mouse, a voice transmission or a data transmission device. Once the input data is acquired in the evaluation module, the patient-specific data, such as the type and number of the imaging units present at the treatment location, can be further used with different patients at each further session. The imaging units that are used for repositioning the patient at the further sessions are, for example, a computer tomography, a magnetic resonance unit, a positron emission tomography or an X-ray system. Patient-specific data which comprise variables characterizing the patient and/or the tumor are also logged. Examples of these are, for example, the type of the affected tissue, the position and size of the tumor, the weight of the patient, his bodily constitution or his age.

The evaluation module has an arithmetic logic unit (processor) and a memory. A functional relationship is stored in the memory. The functional relationship corresponds to a database in which there are stored combinations and parameters, based on experience, for imaging, and correlations thereof with the input data. The input data can be used in this case to determine an imaging plan that, for example, includes the type, the frequency and the parameters for setting the imaging unit to be used. The parameters for setting the imaging unit are the technical parameters of the unit and include the alignment, the energy used, focusing depth or the distance at which the image is taken. The parameters are set such that it is possible to take quality images that fulfill the requirements placed on accuracy. The output data are made available for the medical staff, for example, by being output via a display screen or a printer. The determination of the imaging plan by the evaluation module is performed more quickly and is affected by fewer errors than a determination carried out by a person taking account of empirical values written down.

In one embodiment, the functional relationship is changed in the evaluation module. The change can include a supplementing of the database and a change in the correlations between input data and output data. Consequently, the functional relationship is continuously updated on the basis of dedicated experience, and the updating leads to an improvement in the method for setting up an imaging plan.

In one embodiment, the change in the functional relationship is determined by taking account of the results of the imaging obtained with the aid of the output data. If the output data determined by the evaluation module prove not to be optimum for the prescribed input data, the functional relationship is appropriately changed or supplemented. Newly stored empirical data of optimum results and correlations have a higher output priority than the settings originally determined by the evaluation module, and so the data are output in an optimized fashion in the case of repeated planning using the same input data.

An image data record that is used to change the treatment parameters is advantageously obtained by the imaging unit to be used. Images of the tumor that support the treatment are taken in order to obtain important information relating to its recession. The image data record supplies data relating to possible variations in the bodily state of the patient. In order to achieve effective results without possible side effects on the patient, the changes in the tumor or the patient are taken into account when planning the treatment, and this leads to an adaptation of the treatment parameters.

The treatment parameters are calculated by a comparison of the image data record and an original basic image data record. The three-dimensional basic image data record is obtained at the start of the treatment, in particular with a computer tomograph, and provides detailed information relating to the tumor. The detailed information is used in the course of the therapy as a reference source for the further supporting images. The image data records that are obtained during the therapy are compared with the basic image data record in order to detect deviations in the position of the patient, because such deviations complicate a targeted irradiation of the diseased tissue.

The input data, which may include the type and number of the irradiation devices present, and the output data for a treatment plan are determined in the evaluation module. The imaging plan is a part of the treatment plan that includes, for example, additional settings of the irradiation devices.

In one embodiment, the evaluation module may exchange data with the imaging units and/or irradiation devices via a network. Connecting all the existing units in a network with the evaluation module is attended by the advantage of enabling the parameters of the units to be changed automatically under the control of the evaluation module. The network reduces the human outlay both for the treatment planing and for carrying out the imaging and irradiating the tumor.

A dry (non-irradiating test) run of the imaging unit to be used may be simulated by the evaluation module. During the dry (test) run, the unit used for imaging is brought into the position in which it is intended to take the supporting image of the tumor. The unit is checked whether it collides on its path with other devices or catches the patient and injures him. The checking can be calculated by the evaluation module with the aid of the present method. Account is also taken here of the size of the patient positioned on the couch (support), and the movement sequence of the imaging unit is calculated. A warning is output if the unit collides with other devices as it moves, or catches the patient. The evaluation model is then used to calculate a new movement path.

In one embodiment, a device for planning an irradiation is provided. The device includes an evaluation module with an input for receiving input data, a memory and an output for outputting determined output data. The evaluation module is designed for using the input data that includes the type and number of the imaging units present, variables characterizing the tumor and/or variables characterizing the patient, in order to determine the output data that includes the type of the imaging unit, the frequency of use of the imaging unit and/or the parameters for setting the imaging unit to be used in the form of an imaging plan with the aid of a functional relationship, which is based on experience, stored in the memory.

BRIEF DESCRIPTION OF THE DRAWING

FIG. 1 illustrates a block diagram of a method for planning a treatment.

DETAILED DESCRIPTION

FIG. 1 illustrates a sequence of a method for planning a treatment of a patient's tumor. The patient is positioned on a couch, and imaging units are used to take images of his diseased tissue, and evaluate the images. The images, which are recorded in an image data record 1, are used to draw up (determine) an imaging plan 2 that is part of the therapy. The imaging plan 2 is used to ensure that it is precisely the tissue affected by the tumor that is irradiated during radiation or particle therapy.

A device 3 is used to carry out the method. The device 3 includes an evaluation module 4 that has an input 5 and an output 6. Input data 7 are logged via the input 5, which is, for example, a keypad, a mouse, a voice transmission or a data transmission device. The input data 7 includes three blocks 8, 9, 10 in this exemplary embodiment. The block 8 includes the patient-nonspecific data, such as the type and number of the imaging units present at the treatment location. The imaging units can be a computer tomography device, a magnetic resonance unit, a positron emission tomography device or an X-ray system. The block 9 includes the patient-specific data such as the sizes characterizing the tumor, for example, position and size of the tumor and type of the diseased tissue, as well as the variables characterizing the patient, for example, his age, size, body weight or bodily condition. The type and number of the irradiation devices present may be taken into account in the planning, and this is indicated by block 10.

The logged input data 7 are evaluated in the evaluation module 4. The evaluation module 4 has an arithmetic logic unit 11, such as a processor for electronic data processing, and a memory 12 for storing data. The memory 12 stores a functional relationship 13 with the aid of which the evaluation of the input data 7 and the drawing up of the imaging plan 2 are performed. The functional relationship 13 corresponds (relates) to a database that contains combinations based on experience and parameters for imaging. Correlations are determined in the evaluation module 4 between the input data 7 and the stored data that serve for drawing up the imaging plan 2.

Determined output data 14 are made available to the medical staff via the output 6. The output 6 can be a display screen, a printer or another device for data output. The imaging plan 2, which is drawn up (determined) by the evaluation module 4 and that is a part of a treatment plan 15, includes, for example, the type and frequency of the imaging unit to be used, and the parameters for setting this unit. The parameters of the imaging unit are, for example, alignment, energy used, or focusing depth.

The images obtained with the imaging plan 2 are stored as an image data record 1 and compared with a basic image data record 16. The basic image data record 16 is formed at the start of the treatment by an imaging method for producing three-dimensional images, such as computer tomography. The basic image data record 16 is stored on a data medium accessible to the evaluation module 4, which data medium can be the memory 12 of the evaluation module 4. If, in the course of the treatment, substantial variations are detected in the size and/or the position of the tumor, 3D images can be taken anew and continue to be used as basic image data record 16. The comparison of the image data record 1 with the basic image data record 16 supplies information relating to the development or recession of the tumor, which are of significance for the treatment.

The functional relationship 13 can be changed by medical staff. The changes include both a supplementing of the database and the setting up of new correlations between the input data 7 and the output data 14. Should it turn out that the output data 14 calculated by the evaluation module 4 are not optimal for imaging, the functional relationship 13 can be supplemented by data that had been obtained from dedicated experience. Such supplementary empirical parameter values and settings can be assigned a higher output priority. The change can be carried out in an automated fashion by appropriately networking the participating units.

The present method for planning the treatment of the patient provides a high degree of planning automation that substantially lowers the human outlay during planning. Planning automation can be achieved by an electronic patient file in which, for examples the basic image data record 16, the patient-specific and patient-nonspecific data 8, 9 are stored. During subsequent sessions, further images are taken and are compared to the stored basic image data record 16. This comparison supplies information on whether the repositioning of the patient is required in order to carry out the irradiation of the tumor.

It is possible during the irradiation to use a positron emission tomography that images the biochemical and physiological processes. The use of a number of units for imaging necessitates a dry run that is carried out virtually by the evaluation module 4. During the simulation of the dry run, the positions and movement sequences of all the units required for the imaging are determined computationally. Experimental determination of the movement sequences of a number of units may be too complicated, and so complicated tests in which a number of units are moved into their positions of use are no longer required.

The invention claimed is:

1. A method for planning a treatment of a tumor of a patient in the case of particle, radiation, or particle and radiation therapy, the method comprising:
    determining, in an evaluation module, output data based on input data using a functional relationship based on experience, the functional relationship being stored in a memory, the input data including a type of imaging unit present and a number of the imaging units present, variables characterizing the tumor, variables characterizing the patient, or combinations thereof, the output data being for an imaging plan to take images of the tumor during treatment and comprising the type of the imaging unit, a frequency of use of the imaging unit, parameters for setting the imaging unit, or combinations thereof; and
    determining the imaging plan as part of the therapy based on the determined output data; and
    obtaining an image data record by the imaging unit to be used, the image data record being used to change treatment parameters.

2. The method as claimed in claim 1, further comprising changing the functional relationship in the evaluation module.

3. The method as claimed in claim 2, wherein the change in the functional relationship is determined based on results of images obtained with the output data.

4. The method as claimed in claim 1, wherein the treatment parameters are calculated by comparing the image data record and an original basic image data record.

5. The method as claimed in claim 1, wherein the input data includes a type and number of irradiation devices present, and output data for a treatment plan is determined in the evaluation module.

6. The method as claimed in claim 5, wherein the evaluation module exchanges data with the imaging units, the irradiation devices, or the imaging units and the irradiation devices via a network.

7. The method as claimed in claim 1, further comprising simulating, by the evaluation module, a dry run of the imaging unit to be used.

8. A device for planning a treatment of a tumor of a patient in the case of particle, radiation, or particle and radiation therapy, the device comprising:
    an evaluation module with an input operable to receive input data, a memory and an output operable to output determined output data,
    wherein the evaluation module is operable to determine the output data using the input data, the input data comprising a type and number of imaging units present, variables characterizing the tumor, variables characterizing the patient, or combinations thereof, the output data comprising the type of the imaging unit, a frequency of use of the imaging unit, parameters for setting the imaging unit, or combinations thereof to be used in an imaging plan to take images of the tumor, the evaluation module operable to use a functional relationship based on experience and stored in the memory to determine the imaging plan as part of the therapy, and
    wherein the evaluation module is operable to process a type and number of irradiation devices included as input data, and to output data for a treatment plan.

9. The device as claimed in claim 8, wherein the evaluation module is operable to change the functional relationship.

10. The device as claimed in claim 9, wherein the evaluation module is operable to change the functional relationship by taking account of imaging results obtained with the output data.

11. The device as claimed in claim 8, wherein the evaluation module is connected via a network to the imaging units, the irradiation devices, or the imaging units and the irradiation devices.

12. The device as claimed in claim 8, wherein the evaluation module is operable to determine a dry run of the imaging unit to be used.

* * * * *